(12) United States Patent
Mehta et al.

(10) Patent No.: US 12,070,330 B2
(45) Date of Patent: Aug. 27, 2024

(54) SYSTEMS AND METHODS OF A HEALTH MONITORING DEVICE

(71) Applicant: Smardii, Inc., Miami, FL (US)

(72) Inventors: Vikram S. Mehta, Wayne, NJ (US); Sebastien Gaddini, Upper Holland, PA (US); Mrugesh Patel, Somerset, NJ (US); Mathieu Gaddini, Le Pradet (FR)

(73) Assignee: SMARDII, INC., Miami, FL (US)

(*) Notice: Subject to any disclaimer, the term of this patent is extended or adjusted under 35 U.S.C. 154(b) by 461 days.

(21) Appl. No.: 16/638,926

(22) PCT Filed: Sep. 6, 2018

(86) PCT No.: PCT/US2018/049793
§ 371 (c)(1),
(2) Date: Feb. 13, 2020

(87) PCT Pub. No.: WO2019/051118
PCT Pub. Date: Mar. 14, 2019

(65) Prior Publication Data
US 2020/0222002 A1    Jul. 16, 2020

Related U.S. Application Data

(60) Provisional application No. 62/555,563, filed on Sep. 7, 2017.

(51) Int. Cl.
*A61B 5/00* (2006.01)
*A61B 5/01* (2006.01)
(Continued)

(52) U.S. Cl.
CPC .......... *A61B 5/6808* (2013.01); *A61B 5/0022* (2013.01); *A61B 5/01* (2013.01);
(Continued)

(58) Field of Classification Search
CPC ....... A61B 5/6808; A61B 5/0022; A61B 5/01; A61B 5/02055; A61B 5/02438;
(Continued)

(56) References Cited

U.S. PATENT DOCUMENTS 4,191,950 A    3/1980 Levin et al.
4,768,023 A    8/1988 Xie
(Continued)

FOREIGN PATENT DOCUMENTS

CA    2992409 A1    1/2017
CN    106176054 A    12/2016
(Continued)

OTHER PUBLICATIONS

International Preliminary Report on Patentability, issued Mar. 10, 2020, for PCT Application No. PCT/US2018/049793, 18 pages.
(Continued)

*Primary Examiner* — David J. McCrosky
*Assistant Examiner* — Clarissa Cuevas
(74) *Attorney, Agent, or Firm* — MORRISON & FOERSTER LLP (57) ABSTRACT

Disclosed are systems and methods of a health monitoring device comprising: a flexible circuit, an absorbent product, and, a processing unit. The flexible circuit comprises: an electrochemical biosensor, a color sensor, an LED, and, a moisture sensor. The electrochemical biosensor comprises a plurality of reference electrodes. The processing unit comprises: a GPS antenna, a power unit, a BLUETOOTH® low energy transceiver, a GPS transceiver, a microcontroller, and, an accelerometer. The processing unit is electronically coupled to the flexible circuit. The methods comprise: obtaining health data from health monitoring device; recording the health data on the memory unit; transmitting the
(Continued)

health data to a data communication device; and, displaying the health data on the data communication device.

12 Claims, 7 Drawing Sheets

(51) Int. Cl.
| | |
|---|---|
| *A61B 5/0205* | (2006.01) |
| *A61B 5/024* | (2006.01) |
| *A61B 5/11* | (2006.01) |
| *A61B 5/145* | (2006.01) |
| *A61B 5/1477* | (2006.01) |
| *A61B 5/20* | (2006.01) |
| *A61F 13/42* | (2006.01) |
| *A61F 13/84* | (2006.01) |

(52) U.S. Cl.
CPC ...... *A61B 5/02055* (2013.01); *A61B 5/02438* (2013.01); *A61B 5/1112* (2013.01); *A61B 5/14507* (2013.01); *A61B 5/14532* (2013.01); *A61B 5/1477* (2013.01); *A61B 5/207* (2013.01); *A61F 13/42* (2013.01); *A61B 2562/0219* (2013.01); *A61B 2562/0271* (2013.01); *A61B 2562/029* (2013.01); *A61B 2562/166* (2013.01); *A61F 2013/422* (2013.01); *A61F 2013/424* (2013.01); *A61F 2013/8473* (2013.01); *A61F 2013/8479* (2013.01); *A61F 2013/8488* (2013.01)

(58) Field of Classification Search
CPC .............. A61B 5/1112; A61B 5/14507; A61B 5/14532; A61B 5/1477; A61B 5/207; A61B 2562/0219; A61B 2562/0271; A61B 2562/029; A61B 2562/166; A61B 5/1032; A61B 5/1455; A61F 2013/424; A61F 13/42; G01N 27/12; G01N 27/327
See application file for complete search history.

(56) References Cited

U.S. PATENT DOCUMENTS

| | | | |
|---|---|---|---|
| 6,559,772 | B2 | 5/2003 | Zand et al. |
| 7,141,715 | B2 | 11/2006 | Shapira |
| 7,755,497 | B2 | 7/2010 | Wada et al. |
| 7,977,529 | B2 | 7/2011 | Bergman et al. |
| 8,431,766 | B1 | 4/2013 | Lonero |
| 8,698,641 | B2 | 4/2014 | Abraham et al. |
| 8,975,465 | B2 | 3/2015 | Hong et al. |
| 9,224,102 | B2 | 12/2015 | Barda et al. |
| 9,937,081 | B2 | 4/2018 | Zand |
| 10,335,326 | B2 | 7/2019 | Wu |
| 10,478,349 | B2 | 11/2019 | Mancini et al. |
| 10,722,405 | B2 | 7/2020 | Pepin et al. |
| 11,197,785 | B2 | 12/2021 | Mehta et al. |
| 2007/0179356 | A1 | 8/2007 | Wessel |
| 2007/0270774 | A1 | 11/2007 | Bergman et al. |
| 2008/0167572 | A1 | 7/2008 | Stivoric |
| 2012/0109087 | A1 | 5/2012 | Abraham et al. |
| 2014/0200538 | A1 | 7/2014 | Euliano |
| 2015/0042489 | A1 | 2/2015 | Avon |
| 2015/0180355 | A1 | 6/2015 | Freeman |
| 2016/0029957 | A1 | 2/2016 | Faybishenko et al. |
| 2016/0095758 | A1 | 4/2016 | Haire |
| 2017/0065464 | A1* | 3/2017 | Heil ...................... A61B 5/202 |
| 2018/0011080 | A1 | 1/2018 | Xu |
| 2018/0104114 | A1* | 4/2018 | Pepin .................. G01N 27/048 |
| 2018/0177644 | A1 | 6/2018 | Tuli |
| 2020/0088701 | A1 | 3/2020 | Jung et al. |
| 2020/0337880 | A1 | 10/2020 | Hansen et al. |
| 2021/0205150 | A1 | 7/2021 | Mehta et al. |
| 2021/0401636 | A1 | 12/2021 | Lee |
| 2022/0117802 | A1 | 4/2022 | Mehta et al. |
| 2023/0035397 | A1 | 2/2023 | Mehta et al. |

FOREIGN PATENT DOCUMENTS

| | | |
|---|---|---|
| EP | 2803342 A1 | 11/2014 |
| EP | 2582341 B1 | 4/2016 |
| JP | H10314202 A | 12/1998 |
| JP | 2002143199 A | 5/2002 |
| JP | 2007135862 A | 6/2007 |
| JP | 2008531137 A | 8/2008 |
| JP | 2010502249 A | 1/2010 |
| JP | 2010512942 A | 4/2010 |
| JP | 2012105839 A | 6/2012 |
| JP | 2016500015 A | 1/2016 |
| WO | 2006089377 A1 | 8/2006 |
| WO | 2008026092 A1 | 3/2008 |
| WO | 2008079060 A1 | 7/2008 |
| WO | 2013013197 A1 | 1/2013 |
| WO | 2014064680 A1 | 5/2014 |
| WO | 2016207799 A1 | 12/2016 |
| WO | 2021138459 A1 | 7/2021 |

OTHER PUBLICATIONS

International Search Report and Written Opinion, dated Jan. 7, 2019, for PCT Application No. PCT/US2018/049793, 26 pages.
International Search Report and Written Opinion, dated Apr. 29, 2021, for PCT Application No. PCT/US2020/067525, 11 pages.
Invitation To Pay Additional Fees, mailed Mar. 3, 2021, for PCT Application No. PCT/US2020/067525, filed Dec. 30, 2020, 3 pages.
Extended European Search Report, dated Oct. 11, 2023, for European Patent Application No. 20909734.4, 10 pages.

* cited by examiner

SYSTEMS AND METHODS OF A HEALTH MONITORING DEVICE

CROSS-REFERENCE TO RELATED APPLICATIONS

This application is a National Phase application under 35 U.S.C. § 371 of International Application No. PCT/US2018/049793, filed Sep. 6, 2018, which claims priority to U.S. Provisional Application No. 62/555,563, entitled "SYSTEMS AND METHODS OF A HEALTH MONITORING SYSTEM" filed Sep. 7, 2017, the content of which are hereby incorporated by reference in their entirety for all purposes.

BACKGROUND OF THE INVENTION

The present invention is in the technical field of biomedical technologies. More particularly, the invention is in the technical field of biomedical disposable sensor and digital health device attached to disposable and non-disposable diapers. Conventional diapers do not warn parents, users, and caregivers about any stage of wet and/or soiled diapers. Conventional diapers also do not gather, analyze, process and provide any medical information contained in body fluids whatsoever.

BRIEF SUMMARY OF THE INVENTION

An object of the present invention is a health monitoring device comprising: a flexible circuit, an absorbent product, and, a processing unit. The flexible circuit comprises: an electrochemical biosensor, a color sensor, an LED, and, a moisture sensor. The electrochemical biosensor comprises a plurality of reference electrodes. The processing unit comprises: a GPS antenna, a power unit, a low energy transceiver for wirelessly receiving short range radio waves, such as a BLUETOOTH® low energy transceiver, a GPS transceiver, a microcontroller, and, an accelerometer. The processing unit is electronically coupled to the flexible circuit.

Another object of the present invention is a health monitoring device, wherein the flexible circuit further comprises: a temperature sensor, a humidity sensor, and, a heart rate sensor.

Yet, another object of the present invention is a health monitoring device, wherein the processing unit further comprises: a temperature sensor, a humidity sensor, and, a heart rate sensor.

Another object of the present invention is a health monitoring device, wherein each of the plurality of reference electrodes detects an analyte selected from the group consisting of albumin, ascorbic acid, bilirubin, blood, creatinine, glucose, hemoglobin, ketones, leukocytes, microalbumin, myoglobin, nitrite, pH, protein, specific gravity, urea, uric acid, urobilinogen, vitamins, and combinations thereof.

Yet another object of the present invention is a health monitoring device, further comprising a data communication device.

Another object of the present invention is a health monitoring device, wherein the processing unit further comprises an input/output device connection port, wherein the input/output device connection port electronically couples a secondary monitoring device to the processing unit.

Yet another object of the present invention is a health monitoring device, wherein the secondary monitoring device is selected from the group consisting of pulse oximeters, blood pressure monitors, blood glucose meters, blood coagulation meters, blood oxygen monitor, thermometers, apnea monitors, electrocardiogram monitors, fetal monitors, hemoglobin trackers, breathalyzers, capnography monitors, fitness monitors, pedometers, medical monitors, vital sign monitors, cardiac monitors, hemodynamic monitors, respiratory monitors, neurological monitors, body temperature monitors, heart rate monitors, respiratory rate monitors, stress monitors, serotonin biosensors, epilepsy monitors, toxicity monitors, mercury monitors, lead monitors, biosensors, electrochemical biosensors, moisture sensors, temperature sensors, humidity sensors, color sensors, heart rate sensors, accelerometers, and combinations thereof.

Another object of the present invention is a health monitoring device, wherein the secondary monitoring device is a blood oxygen monitor.

Yet another object of the present invention is a health monitoring device, wherein the flexible circuit and the processing unit are reusable, and, wherein the health monitoring device further comprises an adhesion means to adhere the flexible circuit and the processing unit to the absorbent product.

Another object of the present invention is a health monitoring device, wherein the flexible circuit and the processing unit are disposable.

Yet another object of the present invention is a health monitoring device, wherein the flexible circuit is integrally formed with the absorbent product.

Another object of the present invention is a health monitoring device comprising: a flexible circuit, an absorbent product, and, a processing unit. The flexible circuit comprises: an electrochemical biosensor, a color sensor, an LED, and, a moisture sensor. The electrochemical biosensor comprises a plurality of reference electrodes. The processing unit comprises: a GPS antenna, a power unit, a BLUETOOTH® low energy transceiver, a GPS, transceiver, a microprocessor, a ROM chip, a RAM chip, an analog to digital converter, a digital to analog converter, a serial peripheral interface, a universal asynchronous receiver/transmitter, a power regulator, and, an accelerometer. The processing unit is electronically coupled to the flexible circuit.

Another object of the present invention is a computer system comprising: at least one processor unit; at least one memory unit coupled to the at least one processor unit; and, computer readable instructions embodied in the memory unit and executable by the processor unit, wherein execution of the instructions by the processor unit causes the computing system to perform a method of monitoring the health of a user of a health monitoring device. The method comprising: obtaining health data from health monitoring device; recording the health data on the memory unit; transmitting the health data to a data communication device; and, displaying the health data on the data communication device. The health monitoring device comprises: a flexible circuit, an absorbent product, and, a processing unit. The flexible circuit comprises: an electrochemical biosensor, a color sensor, an LED, and, a moisture sensor. The electrochemical biosensor comprises a plurality of reference electrodes. The processing unit comprises: a GPS antenna, a power unit, a BLUETOOTH® low energy transceiver, a GPS transceiver, a microcontroller, and, an accelerometer. The processing unit is electronically coupled to the flexible circuit.

Yet another object of the present invention is a computer system, wherein the health monitoring device further comprises a blood oxygen monitor, wherein the blood oxygen monitor is electronically coupled to the flexible circuit.

Another object of the present invention is a computer system, wherein the obtaining, recording, transmitting and displaying the health data are repeatedly performed at regular, predefined intervals.

Yet another object of the present invention is a computer system, the method further comprising providing alerts if the health data falls outside of predefined levels.

Another object of the present invention is a computer system, the method further comprising providing alerts if the rate of change of health data falls outside of predefined rates.

Another object of the present invention is a method of monitoring the health of a user of a health monitoring device, the method comprising: obtaining health data from health monitoring device; recording the health data on the memory unit; transmitting the health data to a data communication device; and, displaying the health data on the data communication device. The health monitoring device comprises: a flexible circuit, an absorbent product, and, a processing unit. The flexible circuit comprises: an electrochemical biosensor, a color sensor, an LED, and, a moisture sensor. The electrochemical biosensor comprises a plurality of reference electrodes. The processing unit comprises: a GPS antenna, a power unit, a BLUETOOTH® low energy transceiver, a GPS transceiver, a microcontroller, and, an accelerometer. The processing unit is electronically coupled to the flexible circuit.

Yet another object of the present invention is a method of monitoring the health of a user of a health monitoring device, wherein the health monitoring device further comprises a blood oxygen monitor, wherein the blood oxygen monitor is electronically coupled to the flexible circuit.

Another object of the present invention is a method of monitoring the health of a user of a health monitoring device, wherein the obtaining, recording, transmitting and displaying the health data are repeatedly performed at regular, predefined intervals.

Yet another object of the present invention is a method of monitoring the health of a user of a health monitoring device, the method further comprising providing alerts if the health data falls outside of predefined levels.

Another object of the present invention is a method of monitoring the health of a user of a health monitoring device, the method further comprising providing alerts if the rate of change of health data falls outside of predefined rates.

Another object of the present invention is a non-transitory computer readable medium having computer readable instructions embodied therein, the computer readable instructions being configured to implement a method of monitoring the health of a user of a health monitoring device when executed, the method comprising: obtaining health data from health monitoring device; recording the health data on the memory unit; transmitting the health data to a data communication device; and, displaying the health data on the data communication device. The health monitoring device comprises: a flexible circuit, an absorbent product, and, a processing unit. The flexible circuit comprises: an electrochemical biosensor, a color sensor, an LED, and, a moisture sensor. The electrochemical biosensor comprises a plurality of reference electrodes. The processing unit comprises: a GPS antenna, a power unit, a BLUETOOTH® low energy transceiver, a GPS transceiver, a microcontroller, and, an accelerometer. The processing unit is electronically coupled to the flexible circuit.

Yet another object of the present invention is a non-transitory computer readable medium, wherein the health monitoring device further comprises a blood oxygen monitor, wherein the blood oxygen monitor is electronically coupled to the flexible circuit.

Another object of the present invention is a non-transitory computer readable medium, wherein the obtaining, recording, transmitting and displaying the health data are repeatedly performed at regular, predefined intervals.

Yet another object of the present invention is a non-transitory computer readable medium, the method further comprising providing alerts if the health data falls outside of predefined levels.

Another object of the present invention is a non-transitory computer readable medium, the method further comprising providing alerts if the rate of change of health data falls outside of predefined rates.

BRIEF DESCRIPTION OF THE SEVERAL VIEWS OF THE DRAWING

The advantages and features of the present invention will be better understood as the following description is read in conjunction with the accompanying drawings, wherein.

DETAILED DESCRIPTION OF THE INVENTION

Figure 1:
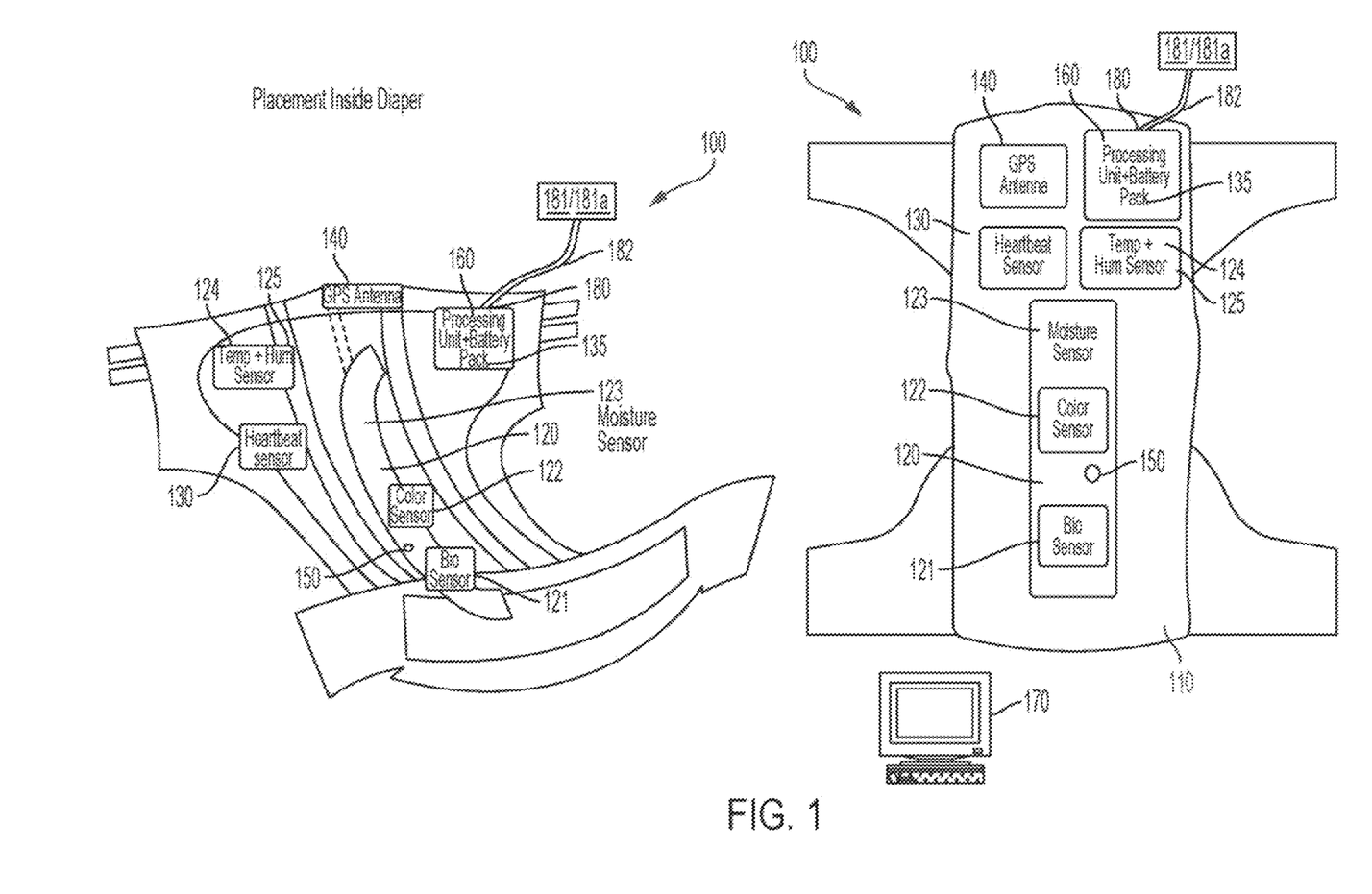
FIG. 1 is a perspective view of an embodiment of the present invention.
Figure 2:
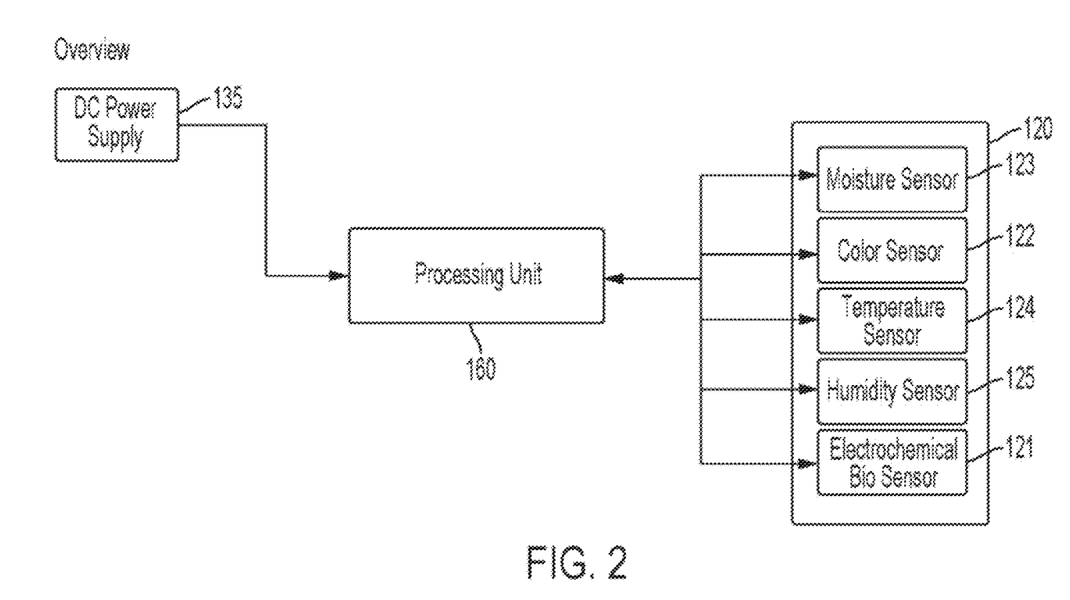
FIG. 2 is an embodiment of the power unit, the processing unit and the flexible circuit of the present invention.

The figures show various embodiments of the present invention. As depicted in FIG. 1, a health monitoring device 100 comprises a flexible circuit 120, an absorbent product 110, and, a processing unit 160. The flexible circuit 120 comprises an electrochemical biosensor 121, a color sensor 122, an LED 150, and, a moisture sensor 123.

Figure 3:
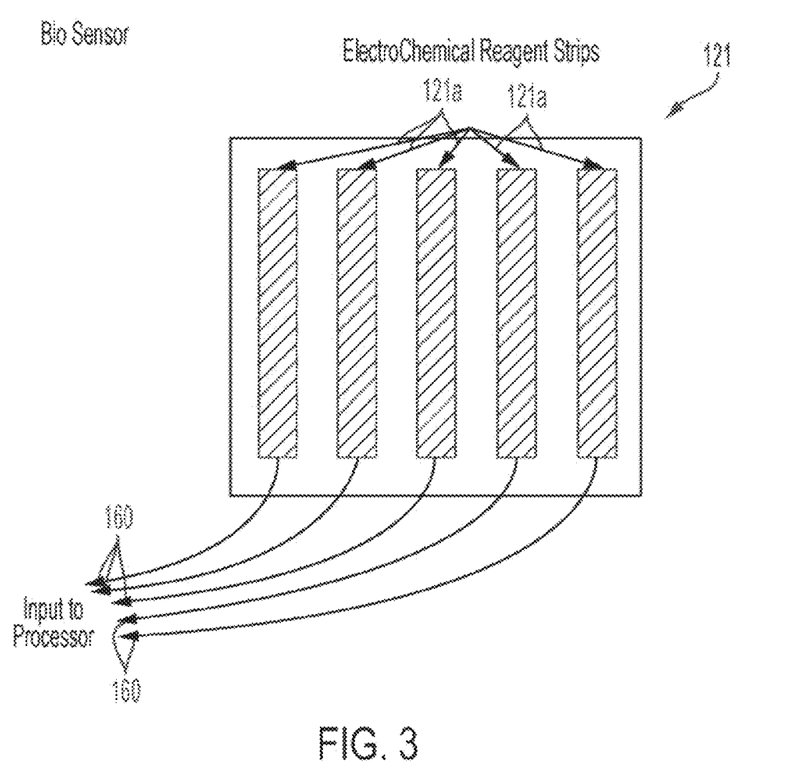
FIG. 3 is an embodiment of the electrochemical biosensor of the present invention.

As shown in FIG. 3, the electrochemical biosensor 121 comprises a plurality of reference electrodes 121a. The plurality of reference electrodes 121 detects an analyte selected from the group consisting of albumin, ascorbic acid, bilirubin, blood, creatinine, glucose, hemoglobin, ketones, leukocytes, microalbumin, myoglobin, nitrite, pH, protein, specific gravity, urea, uric acid, urobilinogen, vitamins, and combinations thereof.

Figure 4A:
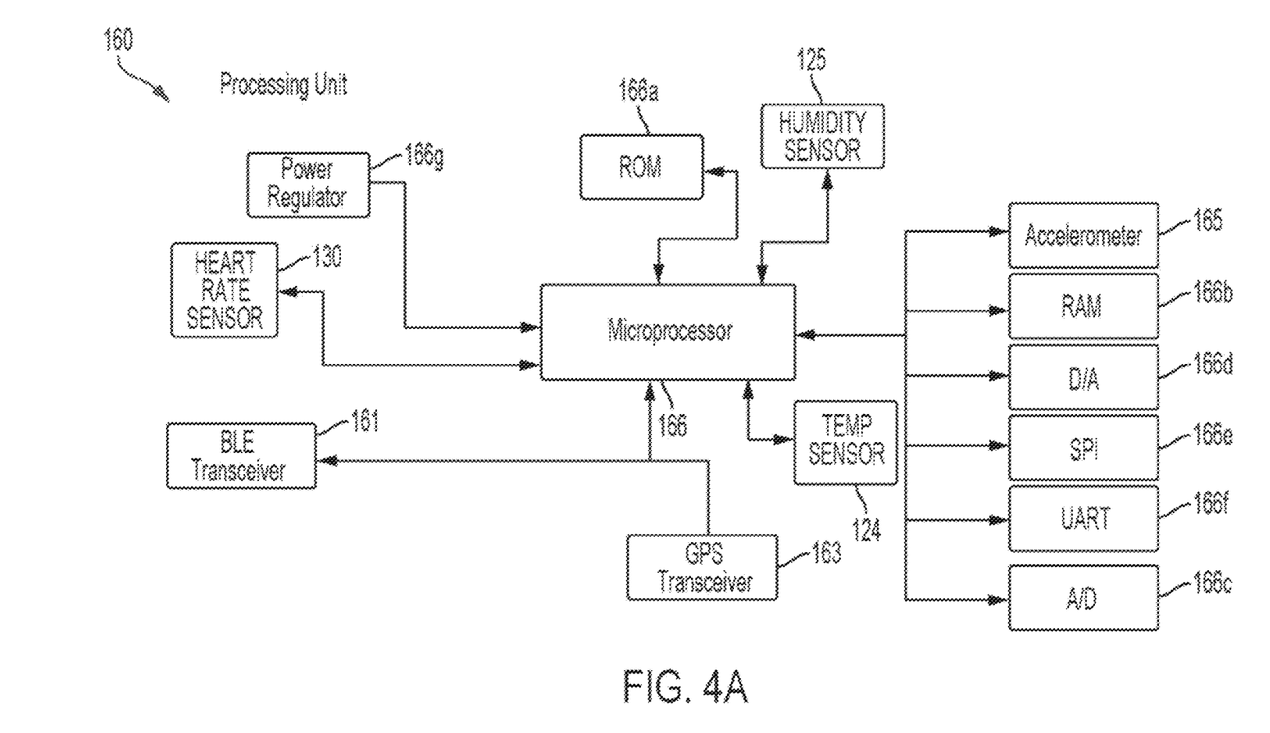
FIG. 4A is an embodiment of the processing unit of the present invention.
Figure 4B:
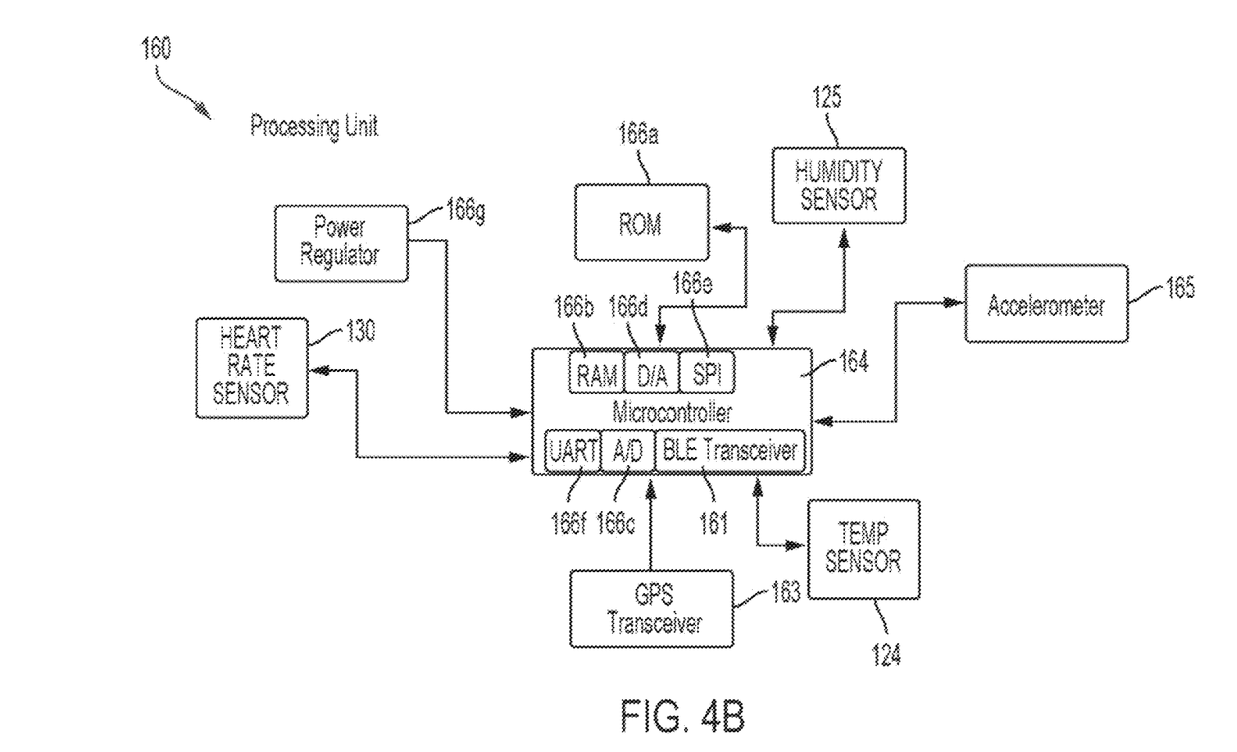
FIG. 4B is an embodiment of the processing unit of the present invention.

As depicted in FIGS. 4A and 4B, the processing unit 160 comprises a GPS antenna 140, a power unit 135, a BLUETOOTH® low energy transceiver 161, a GPS transceiver 163, a microcontroller 164, and, an accelerometer 165. The processing unit 160 is electronically coupled to the flexible circuit 120. In some embodiments the processing unit 160 may communicate wirelessly with the sensors of the flexible circuit 120. BLUETOOTH® low energy is preferred for the safety of the user, as BLUETOOTH® low energy has lower radiation exposure.

In some embodiments, the flexible circuit 120 further comprises a temperature sensor 124, a humidity sensor 125, and, a heart rate sensor 130.

In some embodiments, the processing unit 160 further comprises a temperature sensor 124, a humidity sensor 125, and, a heart rate sensor 130.

In some embodiments, the health monitoring device 100 may further comprise a data communication device 170. The data communication device includes wired and wireless computing devices, such as mobile phones, smart phones, personal computers, laptop computers, tablet computers, or dedicated devices to receive data from the health monitoring device 100.

In some embodiments, the health monitoring device 100 may further comprise an input/output device connection port 180 (as shown in FIG. 1), wherein the input/output device connection port 180 electronically couples a secondary monitoring device 181 to the processing unit 160. A cable that utilizes USB, micro USB, pin connectors, other known electrically coupling connectors known to one skilled in the art, or combinations thereof, may be used to electronically couple the secondary monitoring device 181 to the processing unit 160. An example of a secondary monitoring device 181 is a pulse oximeters 181*a*. In alternative embodiments, the secondary monitoring device 181 does not utilize a cable to communicate with the processing unit 160; instead, the secondary monitoring device 181 may communicate wirelessly (e.g., by BLUETOOTH®) with the processing unit 160. Among the many advantages of wireless communication is not having wires and cables interfering with the user's comfort. Another advantage of wireless communication is that the present invention may utilize numerous secondary monitoring devices 181, and would not be limited to the number of available input/output device connection ports 180.

Other secondary monitoring devices 181 include, but are not limited to, blood pressure monitors, blood glucose meters, blood coagulation meters, blood oxygen monitor, thermometers, apnea monitors, electrocardiogram monitors, fetal monitors, hemoglobin trackers, breathalyzers, capnography monitors, fitness monitors, pedometers, medical monitors, vital sign monitors, cardiac monitors, hemodynamic monitors, respiratory monitors, neurological monitors, body temperature monitors, heart rate monitors, respiratory rate monitors, stress monitors, serotonin biosensors, epilepsy monitors, toxicity monitors, mercury monitors, lead monitors, biosensors, electrochemical biosensors, moisture sensors, temperature sensors, humidity sensors, color sensors, heart rate sensors, accelerometers, and combinations thereof.

In some embodiments, the secondary monitoring device 181 is a blood oxygen monitor 190. The blood oxygen monitor 190 is electronically coupled to the processing unit 160.

In some embodiments, the flexible circuit 120 and the processing unit 160 (including electrochemical biosensor 121, the color sensor 122, the LED 150, the moisture sensor 123, the GPS antenna 140, the power unit 135, the BLUETOOTH® low energy transceiver 161, the GPS transceiver 163, the microcontroller 164, the accelerometer 165, the microprocessor 166, the ROM chip 166*a*, the RAM chip 166*b*, the analog to digital converter 166*c*, the digital to analog converter 166*d*, the serial peripheral interface 166*e*, the universal asynchronous receiver/transmitter 166*f*, the power regulator 166*g*, the temperature sensor 124, the humidity sensor 125, and the heart rate sensor 130) are reusable. The health monitoring device 100 may further comprise an adhesion means to adhere the flexible circuit 120 and the processing unit 160 to the absorbent product 110. The adhesion means include, but is not limited to, adhesive tape, hook and loop fasteners such as VELCRO® brand fasteners, clips, pins, glue, and combinations thereof. In some embodiments, the flexible circuit 120 and the processing unit 160 and their components are waterproof. With regard to the moisture sensor 123, the humidity sensor 125, and the electrochemical sensor 121, these components are waterproof except where the components receive analytes from urine, blood, stool, menses, or combinations thereof.

Figure 5:
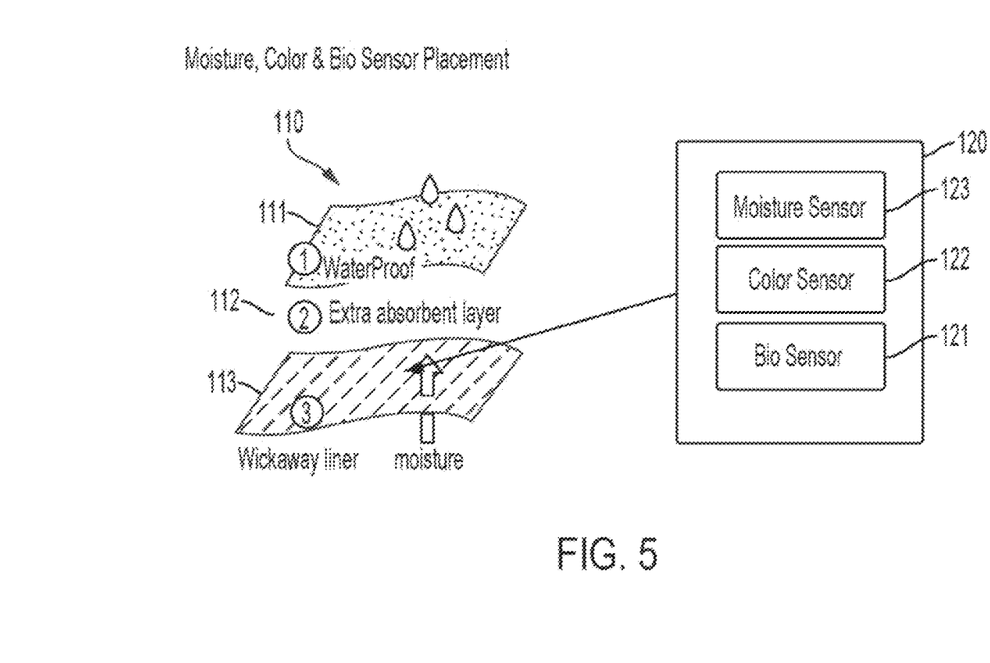
FIG. 5 is an embodiment of the flexible circuit integrally formed with the absorbent product of the present invention.

In other embodiments, the flexible circuit 120 and the processing unit 160 are disposable. In such embodiments, the flexible circuit 120 and the processing unit 160 may be integrally formed with the absorbent product. As shown in FIG. 5, the moisture sensor 123, color sensor 122 and electrochemical biosensor 121 (other disposable components are not depicted for clarity purposes) are inserted in between layers of absorbent product 110.

For example, FIG. 5 shows an example of an absorbent product 110 that includes a waterproof layer 111, an extra absorbent layer 112, and a wickaway liner 113. The components would be inserted between the extra absorbent layer 112, and the wickaway liner 113. The absorbent product 110 shown in FIG. 5 is for illustrative purposes and the present invention is not limited to absorbent products with the illustrated configuration. In some embodiments, the color sensor 122 may detect color changes (due to urine, blood, stool, menses, or combinations thereof) to the extra absorbent layer 112, the wickaway liner 113, or both. For example, the present invention may notify a caretaker that an occurrence of an event (urination, bleeding, a bowel movement, menstruation, or combinations thereof) has occurred. If a user has an event, then the moisture sensor 123, humidity sensor 125, or both, are activated. The activation will indicate to the caretaker that an event has occurred. After the moisture sensor 123, humidity sensor 125, or both, are activated, the color sensor 122 and the LED 150 are triggered to activate to capture the color of the stained extra absorbent layer 112, the wickaway liner 113, or both. The color detected will inform the caretaker whether the event is urination, bleeding, a bowel movement, menstruation, or combinations thereof.

In some embodiments, the processing unit 160 of the health monitoring device 100 comprises, in place or in addition to a microcontroller 164, a microprocessor 166, a ROM chip 166*a*, a RAM chip 166*b*, an analog to digital converter 166*c*, a digital to analog converter 166*d*, a serial peripheral interface 166*e*, a universal asynchronous receiver/transmitter 166*f*, and, a power regulator 166*g*, as shown in FIGS. 4A and 4B.

Figure 6:
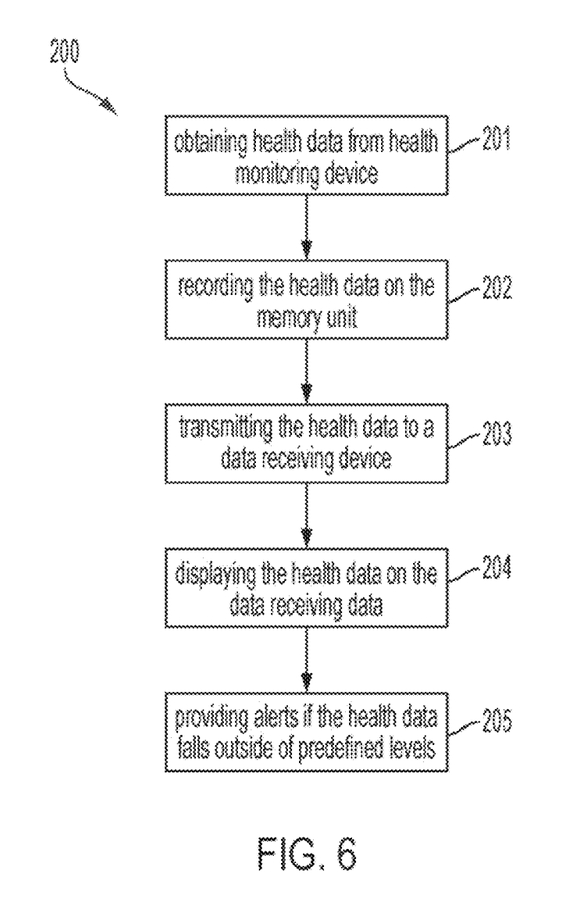
FIG. 6 is an embodiment of one of the methods of the present invention.

In other embodiments of the present invention, a computer system comprises at least one processor unit, at least one memory unit coupled to the at least one processor unit, and, computer readable instructions embodied in the memory unit and executable by the processor unit, wherein execution of the instructions by the processor unit causes the computing system to perform a method of monitoring the health of a user of a health monitoring device 100. The method 200, as illustrated in FIG. 6, comprises obtaining health data from health monitoring device 100, at block 201, recording the health data on the memory unit, at block 202, transmitting the health data to a data communication device 170, at block 203, and, displaying the health data on the data communication device 170, at block 204.

In other embodiments, a method of monitoring the health of a user of a health monitoring device comprises obtaining health data from health monitoring device 100, recording the health data on the memory unit, transmitting the health data to a data communication device 170, and, displaying the health data on the data communication device 170.

In other embodiments, a non-transitory computer readable medium has computer readable instructions embodied therein, the computer readable instructions being configured to implement a method of monitoring the health of a user of a health monitoring device when executed, the method comprises obtaining health data from health monitoring device 100, recording the health data on the memory unit, transmitting the health data to a data communication device 170, and, displaying the health data on the data communication device 170. "Non-transitory computer readable medium" may not include a transitory signal.

In some embodiments, the obtaining, recording, transmitting and displaying the health data are repeatedly performed at regular, predefined intervals.

In some embodiments, the method 200 further comprises providing alerts if the health data falls outside of predefined levels, at block 205. For example, the health monitoring device 100 may be designed with predetermined levels for a certain amount of moisture or humidity (via the moisture sensor 123 and the humidity sensor 125, respectively) to notify a caretaker or the user of the health monitoring device that the absorbent product 110 needs to be replace. The moisture sensor may also be utilized to measure the amount of water in urine. For example, if the amount of water is lower than normal, then it may indicate that more substances in the urine; if the amount of water is greater than normal, then it may indicate that less substances in the urine. Taking body temperature as another example, the average normal body temperature is generally 98.6 degrees fahrenheit. Throughout the day, body temperature will normally range from 97.0 to 99.0 degrees fahrenheit. The predefined levels may be set at 96.5 to 99.5 degrees fahrenheit. As a result, an alert is provided to the caretaker if the body temperature falls below 96.5 or rises above 99.5 degrees fahrenheit. A body temperature over 100.4 degrees fahrenheit often means a fever caused by an infection or illness.

In some embodiments, the method 200 further comprises providing alerts if the rate of change of health data falls outside of predefined rates. Again with body temperature as an example, the average normal body temperature is generally 98.6 degrees fahrenheit. Throughout the day, body temperature will normally range from 97.0 to 99.0 degrees fahrenheit. The predefined rate may be defined at a set rate, for example, +/−0.01 degrees fahrenheit per 5 minutes. As a result, an alert is provided to the caretaker if the rate of change in body temperature changes (increases or decreases) greater than 0.01 degrees every 5 minutes. Alternatively, the predefined rate may be defined by the recording the user's normal change in rate of the user's body temperature. For example, the user's body temperature may normally change+/−0.01 degrees fahrenheit per 10 minutes. As a result, an alert is provided to the caretaker if the rate of change in body temperature changes (increases or decreases) greater than 0.01 degrees every 10 minutes.

The health monitoring device 100 may have predetermined levels for the analytes to be detected by the electrochemical biosensor 121. For example, ranges for the following analytes include:

Albumin and creatinine—a ratio of albumin (mcg/L) to creatinine (mg/L) of less than 30 is normal. A ratio of 30-300 signifies microalbuminuria and ratios above 300 signifies macroalbuminuria. Abnormal levels of creatinine may be indicative of kidney failure, heart attacks, and muscle destruction.

Normal ranges for ascorbic acid are from about 0.6 to about 2 mg/dL. Levels of ascorbic acid that are less than 0.3 mg/dL indicate significant deficiency. Prolonged deficiency may cause scurvy. Excess urine ascorbic acid may be indicative of kidney stones.

Bilirubin is not normally present in urine. Presence of bilirubin in urine is an early indicator of liver disease.

Blood is not normally found in urine. The presence of hemoglobin in the urine may be indicative of hemoglobinuria or hematuria. The presence of myoglobin may be indicative of muscle injury. The presence of blood may also be indicative of kidney disorders and diseases, and urine duct disease.

Glucose is not normally present in urine. Glucosuria is the presence of glucose in urine, which may be the result of excessively high blood glucose levels, a sign of diabetes. Other causes of glucosuria include hormonal disorders, pregnancy, kidney and liver diseases, and diabetes.

Ketones are not normally found in urine. The presence of ketones may be an early indication of insufficient insulin, which may be characteristic of a person with diabetes.

Normal range of urine leukocytes are about 0 to about 5 white blood cells per high power field. High levels of white blood cells may indicate an infection, such as kidney or urinary tract infections.

Normal ranges of microalbumin is from about 20 to about 2000 mg/L. Abnormal levels of microalbumin may be indicative of cardiovascular and kidney diseases.

Urine is normally free of nitrite. Many bacteria can convert nitrate (a normal substance in urine) to nitrite. Therefore, the presence of nitrite in urine may indicate the presence of bacteria or a bacterial infection.

Typical pH values of urine is about pH 6, but may range from about 4.5 to about 8. Because the kidneys play an important role in maintaining acid-base balance of the body, non-typical pH values may indicate kidney problems and acidosis.

Normally, there is no or only a small amount of protein in urine. One of the proteins measured is albumin. Proteinuria is an elevated level of urine protein. Proteinuria may result from fever, stress, and exposure to cold. Protein in urine may also indicate cardiovascular and kidney diseases.

Specific gravity is a measure of urine concentration. A specific gravity of 1.035 indicates concentrated urine, which is urine with substances dissolved in the urine. A high specific gravity (concentrated urine) may be indicative of fever, diarrhea, excessive perspiration, vomiting, hepatic disease, and heart failure. A low specific gravity (diluted urine) may be indicative of antidiuretic hormone deficiency, kidney infections, and calcium and potassium deficiencies.

Urobilinogen is normally present in urine in low concentrations. Urobilinogen levels greater than 1.0 mg/dL may be indicative of liver diseases.

The electrochemical biosensor may detect analytes found in urine, blood, stool and menses.

Preferably, the power unit 135 is a coin battery, a thin disposable bio-safe and environmentally-safe battery, or a rechargeable module. Charging of the power unit 135 may be done by a wired or wireless means.

The LED 150 provides light for the color sensor 122 to get a reading. The LED 150 will turn on for a moment while the color sensor 122 gets a reading and then the LED 150 will turn off. Preferably the LED 150 will be multi-color, for example, an RGBW (red, green, blue & white) LED. The color sensor 122 and the LED 150 may be separate; alternatively, the color sensor 122 may have an LED as part of the color sensor 122.

Preferably, any connecting wires between any of the components of the health monitoring device 100 will be flexible for comfort and fitting purposes of the user.

Exemplary methods, non-transitory computer-readable storage media, systems, and electronic devices are set out in example implementations of the following items:

Item 1. A health monitoring device comprising:
a flexible circuit, wherein the flexible circuit comprises:
an electrochemical biosensor, wherein the electrochemical biosensor comprises a plurality of reference electrodes;
a color sensor; an LED; and.
a moisture sensor:
an absorbent product; and,
a processing unit, wherein the processing unit comprises:
a GPS antenna;
a power unit;
a BLUETOOTH® low energy transceiver; a GPS transceiver;
a microcontroller; and, an accelerometer; wherein the processing unit is electronically coupled to the flexible circuit.

Item 2. The health monitoring device of item 1, wherein the flexible circuit further comprises: a temperature sensor; a humidity sensor; and, a heart rate sensor.

Item 3. The health monitoring device of item 1, wherein the processing unit further comprises: a temperature sensor; a humidity sensor; and,
a heart rate sensor.

Item 4. The health monitoring device of items 2 or 3, wherein each of the plurality of reference electrodes detects an analyte selected from the group consisting of albumin, ascorbic acid, bilirubin, blood, creatinine, glucose, hemoglobin, ketones, leukocytes, microalbumin, myoglobin, nitrite, pH, protein, specific gravity, urea, uric acid, urobilinogen, vitamins, and combinations thereof.

Item 5. The health monitoring device of item 4, further comprising a data communication device.

Item 6. The health monitoring device of item 5, wherein the processing unit further comprises an input/output device connection port, wherein the input/output device connection port electronically couples a secondary monitoring device to the processing unit.

Item 7. The health monitoring device of item 6, wherein the secondary monitoring device is selected from the group consisting of pulse oximeters, blood pressure monitors, blood glucose meters, blood coagulation meters, blood oxygen monitor, thermometers, apnea monitors, electrocardiogram monitors, fetal monitors, hemoglobin trackers, breathalyzers, capnography monitors, fitness monitors, pedometers, medical monitors, vital sign monitors, cardiac monitors, hemodynamic monitors, respiratory monitors, neurological monitors, body temperature monitors, heart rate monitors, respiratory rate monitors, stress monitors, serotonin biosensors, epilepsy monitors, toxicity monitors, mercury monitors, lead monitors, biosensors, electrochemical biosensors, moisture sensors, temperature sensors, humidity sensors, color sensors, heart rate sensors, accelerometers, and combinations thereof.

Item 8. The health monitoring device of item 7, wherein the secondary monitoring device is a blood oxygen monitor.

Item 9. The health monitoring device of item 8, wherein the flexible circuit and the processing unit are reusable; and, wherein the health monitoring device further comprises an adhesion means to adhere the flexible circuit and the processing unit to the absorbent product.

Item 10. The health monitoring device of item 8, wherein the flexible circuit and the processing unit are disposable.

Item 11. The health monitoring device of item 10, wherein the flexible circuit is integrally formed with the absorbent product.

Item 12. A health monitoring device comprising:
a flexible circuit, wherein the flexible circuit comprises:
an electrochemical biosensor, wherein the electrochemical biosensor comprises a plurality of reference electrodes;
a color sensor; an LED; and,
a moisture sensor;
an absorbent product; and,
a processing unit, wherein the processing unit comprises:
a GPS antenna;
a power unit;
a BLUETOOTH® low energy transceiver; a GPS transceiver;
a microprocessor; a ROM chip;
a RAM chip;
an analog to digital converter; a digital to analog converter; a serial peripheral interface;
a universal asynchronous receiver/transmitter; a power regulator; and,
an accelerometer; wherein the processing unit is electronically coupled to the flexible circuit.

Item 13. The health monitoring device of item 12, wherein the flexible circuit further comprises: a temperature sensor; a humidity sensor; and, a heart rate sensor.

Item 14. The health monitoring device of item 12, wherein the processing unit further comprises:
a temperature sensor; a humidity sensor; and, a heart rate sensor.

Item 15. The health monitoring device of items 13 or 14, wherein each of the plurality of reference electrodes detects an analyte selected from the group consisting of albumin, ascorbic acid, bilirubin, blood, creatinine, glucose, hemoglobin, ketones, leukocytes, microalbumin, myoglobin, nitrite, pH, protein, specific gravity, urea, uric acid, urobilinogen, vitamins, and combinations thereof.

Item 16. The health monitoring device of item 15, further comprising a data communication device.

Item 17. The health monitoring device of item 16, wherein the processing unit further comprises an input/output device connection port, wherein the input/output device connection port electronically couples a secondary monitoring device to the processing unit.

Item 18. The health monitoring device of item 17, wherein the secondary monitoring device is selected from the group consisting of pulse oximeters, blood pressure monitors, blood glucose meters, blood coagulation meters, blood oxygen monitor, thermometers, apnea monitors, electrocardiogram monitors, fetal monitors, hemoglobin trackers, breathalyzers, capnography monitors, fitness monitors, pedometers, medical monitors, vital sign monitors, cardiac monitors, hemodynamic monitors, respiratory monitors, neurological monitors, body temperature monitors, heart rate monitors, respiratory rate monitors, stress monitors, serotonin biosensors, epilepsy monitors, toxicity monitors, mercury monitors, lead monitors, biosensors, electrochemical biosensors, moisture sensors, temperature sensors, humidity sensors, color sensors, heart rate sensors, accelerometers, and combinations thereof.

Item 19. The health monitoring device of item 18, wherein the secondary monitoring device is a blood oxygen monitor.

Item 20. The health monitoring device of item 19, wherein the flexible circuit and the processing unit are reusable; and, wherein the health monitoring device further comprises an adhesion means to adhere the flexible circuit and the processing unit to the absorbent product.

Item 21. The health monitoring device of item 19, wherein the flexible circuit and the processing unit are disposable.

Item 22. The health monitoring device of item 21, wherein the flexible circuit is integrally formed with the absorbent product.

Item 23. A computer system comprising: at least one processor unit:
at least one memory unit coupled to the at least one processor unit; and,
computer readable instructions embodied in the memory unit and executable by the processor unit, wherein execution of the instructions by the processor unit causes the computing system to perform a method of monitoring the health of a user of a health monitoring device, the method comprising:
obtaining health data from health monitoring device;
wherein the health monitoring device comprises:
a flexible circuit, wherein the flexible circuit comprises:
an electrochemical biosensor, wherein the electrochemical biosensor comprises a plurality of reference electrodes;
a color sensor;
an LED; and,
a moisture sensor;
an absorbent product; and,
a processing unit, wherein the processing unit comprises:
a GPS antenna;
a power unit;
a BLUETOOTH® low energy transceiver; a GPS transceiver;
a microcontroller; and, an accelerometer:
wherein the processing unit is electronically coupled to the flexible circuit, recording the health data on the memory unit; transmitting the health data to a data communication device; and, displaying the health data on the data communication device.

Item 24. The computer system of item 23, wherein the flexible circuit further comprises: a temperature sensor;
a humidity sensor; and, a heart rate sensor.

Item 25. The computer system of item 23, wherein the processing unit further comprises: a temperature sensor;
a humidity sensor; and, a heart rate sensor.

Item 26. The computer system of items 24 or 25, wherein the health monitoring device further comprises a blood oxygen monitor, wherein the blood oxygen monitor is electronically coupled to the flexible circuit.

Item 27. The computer system of item 26, wherein the obtaining, recording, transmitting and displaying the health data are repeatedly performed at regular, predefined intervals.

Item 28. The computer system of item 27, the method further comprising providing alerts if the health data falls outside of predefined levels.

Item 29. The computer system of item 27, the method further comprising providing alerts if the rate of change of health data falls outside of predefined rates.

Item 30. A method of monitoring the health of a user of a health monitoring device, the method comprising:
obtaining health data from health monitoring device;
wherein the health monitoring device comprises:
a flexible circuit, wherein the flexible circuit comprises:
an electrochemical biosensor, wherein the electrochemical biosensor comprises a plurality of reference electrodes;
a color sensor; an LED; and,
a moisture sensor;
an absorbent product; and,
a processing unit, wherein the processing unit comprises: a GPS antenna;
a power unit;
a BLUETOOTH® low energy transceiver; a GPS transceiver;
a microcontroller; and,
an accelerometer;
wherein the processing unit is electronically coupled to the flexible circuit; recording the health data on the memory unit, transmitting the health data to a data communication device; and, displaying the health data on the data communication device.

Item 31. The method of item 30, wherein the flexible circuit further comprises: a temperature sensor;
a humidity sensor; and,
a heart rate sensor.

Item 32. The method of item 30, wherein the processing unit further comprises: a temperature sensor;
a humidity sensor; and, a heart rate sensor.

Item 33. The method of items of 31 or 32, wherein the health monitoring device further comprises a blood oxygen monitor, wherein the blood oxygen monitor is electronically coupled to the flexible circuit.

Item 34. The method of item 33, wherein the obtaining, recording, transmitting and displaying the health data are repeatedly performed at regular, predefined intervals.

Item 35. The method of item 34, the method further comprising providing alerts if the health data falls outside of predefined levels.

Item 36. The computer system of item 34, the method further comprising providing alerts if the rate of change of health data falls outside of predefined rates.

Item 37. A non-transitory computer readable medium having computer readable instructions embodied therein, the computer readable instructions being configured to implement a method of monitoring the health of a user of a health monitoring device when executed, the method comprising:
obtaining health data from health monitoring device;
wherein the health monitoring device comprises:
a flexible circuit, wherein the flexible circuit comprises:
an electrochemical biosensor, wherein the electrochemical biosensor comprises a plurality of reference electrodes;
a color sensor; an LED; and,
a moisture sensor;
an absorbent product; and,
a processing unit, wherein the processing unit comprises:
a GPS antenna;
a power unit;
a BLUETOOTH® low energy transceiver;
a GPS transceiver;
a microcontroller; and, an accelerometer;
wherein the processing unit is electronically coupled to the flexible circuit; recording the health data on the memory unit; transmitting the health data to a data communication device; and, displaying the health data on the data communication device.

Item 38. The non-transitory computer readable medium of item 37, wherein the flexible circuit further comprises:
a temperature sensor;
a humidity sensor; and,
a heart rate sensor.

Item 39. The non-transitory computer readable medium of item 37, wherein the processing unit further comprises:
a temperature sensor;
a humidity sensor; and,
a heart rate sensor.

Item 40. The non-transitory computer readable medium of items 38 or 39, wherein the health monitoring device further comprises a blood oxygen monitor, wherein the blood oxygen monitor is electronically coupled to the flexible circuit.

Item 41. The non-transitory computer readable medium of item 40, wherein the obtaining, recording, transmitting and displaying the health data are repeatedly performed at regular, predefined intervals.

Item 42. The non-transitory computer readable medium of item 41, the method further comprising providing alerts if the health data falls outside of predefined levels.

Item 43. The computer system of item 11, the method further comprising providing alerts if the rate of change of health data falls outside of predefined rates.

Item 44. A computer-implemented method for monitoring a health condition of an individual, comprising:
  detecting, using a first sensor of a disposable article, an occurrence of an event, wherein the event corresponds to an excretion of bodily waste;
  in response to detecting the occurrence of an event, activating a second sensor of the disposable article, wherein the second sensor is different from the first sensor;
  capturing, using the second sensor, color information associated with the bodily waste,
  based on the captured color information, identifying an event type from a plurality of predefined event types; and
  providing an output indicative of the identified event type.

Item 45. The method of item 44, wherein the event comprises urination, bleeding, menstruation, excretion of other bodily fluids, a bowel movement, passing of gas, or any combination thereof.

Item 46. The method of any of items 44-45, wherein the bodily waste comprises urine, blood, other bodily fluids, feces, gas, or any combination thereof.

Item 47. The method of any of items 44-46, wherein the first sensor comprises a moisture sensor, a humidity sensor, or both.

Item 48. The method of any of items 44-47, wherein the second sensor comprises a color sensor, a LED unit, or a combination thereof.

Item 49. The method of any of items 44-48, wherein capturing color information comprises capturing color information of a portion of the disposable article.

Item 50. The method of any of items 44-49, wherein capturing color information comprises capturing color information of the bodily waste.

Item 51. The method of any of items 44-50, further comprising:
  detecting, using an electrochemical biosensor of the disposable article, a level of an analyte in the bodily waste;
  based on the level of the analyte in the bodily waste, determining a condition of a plurality of predetermined conditions; and
  providing an output indicative of the determined condition.

Item 52. The method of any of items 44-51, further comprising:
  detecting, using a temperature sensor, a temperature reading;
  based on the temperature reading, determining a condition of a plurality of predetermined conditions; and
  providing an output indicative of the determined condition.

Item 53. The method of any of items 44-52, wherein the disposable article further comprises a heart rate monitor.

Item 54. The method of any of items 44-53, wherein the disposable article further comprises an accelerometer or a gyroscope.

Item 55. A non-transitory computer-readable storage medium storing one or more programs, the one or more programs comprising instructions, which when executed by one or more processors of an electronic device having a display, cause the electronic device to:
  detect, using a first sensor of a disposable article, an occurrence of an event, wherein the event corresponds to an excretion of bodily waste;
  in response to detecting the occurrence of an event, activate a second sensor of the disposable article, wherein the second sensor is different from the first sensor;
  capture, using the second sensor, color information associated with the bodily waste;
  based on the captured color information, identify an event type from a plurality of predefined event types; and
  provide an output indicative of the identified event type.

Various exemplary embodiments are described herein. Reference is made to these examples in a non-limiting sense. They are provided to illustrate more broadly applicable aspects of the disclosed technology. Various changes may be made and equivalents may be substituted without departing from the true spirit and scope of the various embodiments. In addition, many modifications may be made to adapt a particular situation, material, composition of matter, process, process act(s) or step(s) to the objective(s), spirit or scope of the various embodiments. Further, as will be appreciated by those with skill in the art, each of the individual variations described and illustrated herein has discrete components and features which may be readily separated from or combined with the features of any of the other several embodiments without departing from the scope or spirit of the various embodiments.

We claim:

1. A computer-implemented method for monitoring a health condition of an individual using a wearable device, wherein the wearable device comprises:
  an absorbent layer,
  a wickaway liner, and
  a sensing circuit positioned between the absorbent layer and the wickaway liner, the
  sensing circuit comprising a first sensor and a second sensor,
  the method comprising:
    detecting, using the first sensor of the sensing circuit, an occurrence of an event, wherein the event corresponds to an excretion of bodily waste;
    in response to detecting the occurrence of the event using the first sensor, activating the second sensor of the sensing circuit, wherein the second sensor is different from the first sensor;
    capturing, using the second sensor, color information on one or more of the absorbent layer and the wickaway liner, the color information indicating a color of the bodily waste, wherein the second sensor is configured to capture color information of solid and non-solid bodily waste;
    receiving health data from the sensing circuit, the health data comprising an indication of the occurrence of the event and the captured color information;

based on the health data, identifying a type of bodily waste corresponding to the event, the type of bodily waste identified from a plurality of predefined types of bodily waste; and providing an output indicative of the event and the identified type of bodily waste.

2. The method of claim 1, wherein the event comprises urination, bleeding, menstruation, excretion of other bodily fluids, a bowel movement, passing of gas, or any combination thereof.

3. The method of claim 1, wherein the type of bodily waste comprises urine, blood, other bodily fluids, feces, gas, or any combination thereof.

4. The method of claim 1, wherein the first sensor comprises a moisture sensor, a humidity sensor, or both.

5. The method of claim 1, wherein the second sensor comprises a color sensor, a LED unit, or a combination thereof.

6. The method of claim 1, wherein capturing the color information comprises capturing color information of a portion of the wearable device.

7. The method of claim 1, wherein capturing the color information comprises capturing color information of the bodily waste.

8. The method of claim 1, wherein the sensing circuit further comprises an electrochemical biosensor, the method further comprising:
   detecting, using the electrochemical biosensor, a level of an analyte in the bodily waste; and
   transmitting the level of the analyte in the bodily waste to a second device, wherein:
   a condition of a plurality of predetermined conditions is determined at the second device based on the level of the analyte in the bodily waste, and
   an output indicative of the determined condition is provided at the second device.

9. The method of claim 1, further comprising:
   detecting, using a temperature sensor, a temperature reading at the wearable device; and
   transmitting the temperature reading to a second device, wherein:
   a condition of a plurality of predetermined conditions is determined at the second device based on the temperature reading; and
   an output indicative of the determined condition is provided at the second device.

10. The method of claim 1, wherein the wearable device further comprises a heart rate monitor.

11. The method of claim 1, wherein the wearable device further comprises one or more of an accelerometer and a gyroscope.

12. A non-transitory computer-readable storage medium storing one or more programs, the one or more programs comprising instructions, which when executed by one or more processors of an electronic device, cause the electronic device to perform a method comprising:
   receiving health data comprising an indication of an occurrence of an event and captured color information from a wearable device, wherein:
   the wearable device comprises:
      an absorbent layer,
      a wickaway liner, and
      a sensing circuit positioned between the absorbent layer and the wickaway liner, the sensing circuit comprising a first sensor and a second sensor, the event corresponds to an excretion of bodily waste, and
   the color information indicates a color of the bodily waste and is on one or more of the absorbent layer and the wickaway liner;
   based on the health data, identifying a type of bodily waste corresponding to the event, the type of bodily waste identified from a plurality of predefined types of bodily waste; and
   providing an output indicative of the event and the identified type of bodily waste, wherein the wearable device is configured to perform a method comprising:
   detecting, using the first sensor of the sensing circuit, the occurrence of the event;
   in response to detecting the occurrence of the event using the first sensor, activating the second sensor of the sensing circuit, wherein the second sensor is different from the first sensor; and
   capturing, using the second sensor, the color information, wherein the second sensor is configured to capture color information of solid and non-solid bodily waste.

* * * * *